US009296769B2

(12) United States Patent
Liu et al.

(10) Patent No.: US 9,296,769 B2
(45) Date of Patent: *Mar. 29, 2016

(54) TENOFOVIR ALAFENAMIDE HEMIFUMARATE

(71) Applicant: Gilead Sciences, Inc., Foster City, CA (US)

(72) Inventors: Dazhan Liu, Edmonton (CA); Bing Shi, Foster City, CA (US); Fang Wang, Foster City, CA (US); Richard Hung Chiu Yu, San Francisco, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/197,873

(22) Filed: Mar. 5, 2014

(65) Prior Publication Data

US 2014/0187773 A1    Jul. 3, 2014

Related U.S. Application Data

(63) Continuation of application No. 13/586,358, filed on Aug. 15, 2012, now Pat. No. 8,754,065.

(60) Provisional application No. 61/524,224, filed on Aug. 16, 2011.

(51) Int. Cl.
| | |
|---|---|
| A61K 31/685 | (2006.01) |
| C07F 9/6561 | (2006.01) |
| A61K 31/52 | (2006.01) |
| C07D 473/34 | (2006.01) |

(52) U.S. Cl.
CPC ............. *C07F 9/65616* (2013.01); *A61K 31/52* (2013.01); *A61K 31/685* (2013.01); *C07D 473/34* (2013.01)

(58) Field of Classification Search
None
See application file for complete search history.

(56) References Cited

U.S. PATENT DOCUMENTS

| | | | |
|---|---|---|---|
| 5,583,149 A | 12/1996 | Cipollina et al. | |
| 5,663,159 A | 9/1997 | Starrett, Jr. et al. | |
| 5,798,340 A | 8/1998 | Bischofberger et al. | |
| 7,390,791 B2 | 6/2008 | Becker et al. | |
| 7,803,788 B2 | 9/2010 | Becker et al. | |
| 7,939,553 B2 | 5/2011 | Desai et al. | |
| 8,067,449 B2 | 11/2011 | Desai et al. | |
| 8,148,374 B2 | 4/2012 | Desai et al. | |
| 8,383,655 B2 | 2/2013 | Desai et al. | |
| 8,486,942 B2 | 7/2013 | Desai et al. | |
| 8,633,219 B2 | 1/2014 | Matsuzaki et al. | |
| 8,664,386 B2 | 3/2014 | Colby et al. | |
| 8,754,065 B2 | 6/2014 | Liu et al. | |
| 9,139,541 B2 | 9/2015 | Desai et al. | |
| 2009/0176983 A1 | 7/2009 | Dova et al. | |
| 2009/0286981 A1 | 11/2009 | Vasireddy et al. | |
| 2010/0189687 A1 | 7/2010 | Desai et al. | |
| 2013/0065856 A1 | 3/2013 | Liu et al. | |
| 2013/0123311 A1 | 5/2013 | Desai et al. | |
| 2014/0017199 A1 | 1/2014 | Desai et al. | |
| 2014/0105859 A1 | 4/2014 | Desai et al. | |
| 2014/0128602 A1 | 5/2014 | Colby et al. | |
| 2015/0011775 A1 | 1/2015 | Desai et al. | |
| 2015/0105350 A1 | 4/2015 | Ramanathan | |
| 2015/0139948 A1 | 5/2015 | Desai et al. | |

FOREIGN PATENT DOCUMENTS

| | | |
|---|---|---|
| AU | 38970/97 A | 2/1998 |
| AU | 85827/97 A | 2/1999 |
| AU | 85827/98 A | 2/1999 |
| AU | 2001282941 B2 | 4/2006 |
| AU | 2013204731 A1 | 8/2013 |
| EC | SP-045074 A | 5/2004 |
| EC | SP-2004-5349 A | 1/2005 |
| EC | SP-2005-5836 A | 8/2005 |
| EC | SP-2010-10636 A | 3/2011 |
| WO | 98/04569 | 2/1998 |
| WO | 02/08241 | 1/2002 |
| WO | WO-03/086367 A1 | 10/2003 |
| WO | WO-2004/050643 A2 | 6/2004 |
| WO | WO-2004/050643 A3 | 6/2004 |
| WO | WO-2007/013086 A1 | 2/2007 |
| WO | WO-2008/010921 A2 | 1/2008 |
| WO | WO-2008/010921 A3 | 1/2008 |
| WO | WO-2008/103949 A1 | 8/2008 |
| WO | WO-2009/135179 A2 | 11/2009 |
| WO | WO-2009/135179 A3 | 11/2009 |
| WO | WO-2010/091197 A2 | 8/2010 |
| WO | WO-2010/091197 A3 | 8/2010 |
| WO | WO-2012/039787 A1 | 3/2012 |
| WO | WO-2012/068535 A1 | 5/2012 |
| WO | WO-2013/116720 A1 | 8/2013 |

OTHER PUBLICATIONS

Aakeroy, C.B. et al. (May-Jun. 2007). "Cocrystal or Salt: Does it Really Matter?" *Mol. Pharm.* 4(3):317-322.
Chen, J. et al. (2011). "Pharmaceutical Crystallization," *Cryst. Growth Des.* 11:887-895.
Childs, S.L. et al. (May-Jun. 2007). "The Salt-Cocrystal Continuum: The Influence of Crystal Structure on Ionization State," *Mol. Pharm.* 4(3):323-338.
Gallant, J.E. et al. (Oct. 1, 2003). "Tenofovir Disoproxil Fumarate," *Clin. Infectious Diseases* 37:944-950.
Lee et al. (2010). "Characterisation and Anisotropic Lattice Expansion/Contraction of Polymorphs of Tenofovir Disoproxil Fumarate," *Crystal Growth & Des.* 10:2314-2322.
O'Neil, M. et al. (2006). "Aliskiren," in *The Merck Index: An Encyclopedia of Chemicals, Drugs, and Biologicals*, Fourteenth Edition, 2 Total Pages.

(Continued)

*Primary Examiner* — James D Anderson
(74) *Attorney, Agent, or Firm* — Morrison & Foerster LLP

(57) ABSTRACT

A hemifumarate form of 9-[(R)-2-[[(S)-[[(S)-1-(isopropoxycarbonyl)ethyl]amino]phenoxyphosphinyl]methoxy]propyl]adenine (tenofovir alafenamide), and antiviral therapy using tenofovir alafenamide hemifumarate (e.g., anti-HIV and anti-HBV therapies).

19 Claims, 4 Drawing Sheets

(56) References Cited

OTHER PUBLICATIONS

O'Neil, M. et al. (2006). "Bisoprolol," in *The Merck Index: An Encyclopedia of Chemicals, Drugs, and Biologicals*, Fourteenth Edition, 2 Total Pages.
O'Neil, M. et al. (2006). "Quetiapine," in *The Merck Index: An Encyclopedia of Chemicals, Drugs, and Biologicals*, Fourteenth Edition, 2 Total Pages.
O'Neil, M. et al. (2006). "Xamoterol," in *The Merck Index: An Encyclopedia of Chemicals, Drugs, and Biologicals*, Fourteenth Edition, 2 Total Pages.
Sarma, B. et al. (2011). "Soiled Forms of Pharmaceuticals: Polymorphs, Salts, and Cocrystals," *Korean J. Chem. Eng.* 28(2):315-332.
Yadav, A.V. et al. (Jul. 2009). "Co-Crystals: A Novel Approach to Modify Physicochemical Properties of Active Pharmaceutical Ingredients," *Indian J. Pharm. Sci.* 71(4):359-370.
Bolivian Office Action mailed on Mar. 20, 2015, for Bolivian Patent Application No. SP02772012, filed on Aug. 15, 2012, eight pages.
U.S. Appl. No. 61/624,676, filed Apr. 16, 2012, by Ramanathan.
Chapman, et al., "Practical Synthesis, Separation, and Stereochemical Assignment of the PMPA Pro-Drug GS-7340", Nucleosides, Nucleotides & Nucleic Acids, vol. 20, No. 4-7 (2001) 621-28.
Chapman, et al., "Purification of PMPA Amidate Prodrugs by SMB Chromotagraphy and X-Ray Crystallography of the Diastereomerically Pure GS-7340", Nucleosides, Nucleotides & Nucleic Acids, vol. 20, No. 4-7 (2001) 1085-90.
Jones, et al., "Minireview: nucleotide prodrugs", Antiviral Research, vol. 27 (1995) 1-17.
McIntee, et al., "Probing the Mechanism of Action and Decomposition of Amino Acid Phosphonnonoester Amidates of Antiviral Nucleoside Prodrugs", J. Med. Chem., vol. 40 (1997) 3323-31.
Statement of Opposition for Venezuelan Patent Application No. 2012-001018, filed on Aug. 15, 2012, 27 pages.
Notice of Opposition for Australian Patent Application No. 2012296622, filed on Dec. 11, 2014, by Alphapharm Pty Limited, 3 pages.
Correa, C. (Jan. 2007). "Guidelines for the Examination of Pharmaceutical Patents: Developing a Public Health Perspective," *WHO, ICTSD and UNCTAD*, sixty-five total pages.
Herrera, D. (Jul.-Sep. 2010). "What Do You Know About Pharmaceutical Co-Crystals?" *Mexican Journal of Pharmaceutical Science* 41(3):55-56.
International Search Report mailed on Oct. 5, 2012, for PCT Patent Application No. PCT/US2012/050920, filed on Aug. 15, 2012, five pages.
Written Opinion of the International Searching Authority mailed on Oct. 5, 2012, for PCT Patent Application No. PCT/US2012/050920, filed on Aug. 15, 2012, six pages.
O'Neil, M. et al. (2013). "Tefonovir," in *The Merck Index: An Encyclopedia of Chemicals, Drugs, and Biologicals*, Fifteenth Edition, pp. 1694-1695.
Bolivian Office Action mailed on Sep. 1, 2014, for Bolivian Patent Application No. SP02772012, filed on Aug. 15, 2012, fifteen pages.
Chinese Office Action mailed on Oct. 10, 2015, for Chinese Patent Application No. 201280039891.0, filed on Aug. 15, 2012, fourteen pages.
Declaration (Second) of Dr. Alan D. Robertson (with Annexure) in the Matter of Australian Patent Application No. 2012296622 and Opposition by Alphapharm Pty Ltd., dated Nov. 16, 2015, forty-eight pages.
Declaration (Second) of Dr. Jonathan A.V. Coates of Avexa Limited in the Matter of Australian Patent Application No. 2012296622 and Opposition by Alphapharm Pty Ltd., dated Nov. 16, 2015, eleven pages.
Non-Final Office Action mailed on Dec. 3, 2015, for U.S. Appl. No. 14/376,116, filed Dec. 12, 2014, nine pages.
Berge, S.M. et al. (Jan. 1977). "Pharmaceutical Salts," *J. Pharm. Sci.* 66(1):1-19.
Brittain, H.G. (2009). *Polymorphism in Pharmaceutical Solids*, Second Edition, Informa Healthcare, CRC Press, pp. 1-4, 15-19 and 318-430.
Declaration of Helen Grimes (with Annexure) in the Matter of Australian Patent Application No. 2012296622 and Opposition by Alphapharm Pty Ltd., dated Jun. 11, 2015, thirty-one pages.
Declaration of Dr. Jonathan A.V. Coates (with Annexure) of Avexa Limited in the Matter of Australian Patent Application No. 2012296622 and Opposition by Alphapharm Pty Ltd., dated Jun. 11, 2015, twenty-three pages.
Declaration of Dr. Alan D. Robertson (with Annexure) in the Matter of Australian Patent Application No. 2012296622 and Opposition by Alphapharm Pty Ltd., dated Jun. 11, 2015, 398 pages.
Declaration of Alistair George Draffan (with Annexure) in the Matter of Australian Patent Application No. 2012296622 and Opposition by Alphapharm Pty Ltd., dated Sep. 11, 2015, fifty-seven pages.
Declaration of Nair Rodriguez-Hornedo (with Annexure) in the Matter of Australian Patent Application No. 2012296622 and Opposition by Alphapharm Pty Ltd., dated Sep. 10, 2015, 134 pages.
Garrido, J. (1973). Chapter 5 in *Form and Structure of Crystals*, Alhambra Publishers, pp. 204 (with English Translation).
Giron, D. (1995). "Thermal Analysis and Calorimetric Methods in the Characterisation of Polymorphs and Solvates," *Thermochimica Acta* 248:1-59.
Morrison, R.T. et al. (Dec. 1976). *Organic Chemistry*, Allyn and Bacon USA, Inc., pp. 769 (with English Machine Translation).
Negre, J.M.S. (2002). Continuing Education—For Pharmacists in Hospital—New Galenic Contributions to the Forms of Directors, 52 Total pages (with English Machine Translation).
Osol, A. et al. (1980). *Remington's Pharmaceutical Sciences*, 16$^{th}$ Edition, Mack Publishing Company, Easton:PA, pp. 180-181.
Wikipedia (Apr. 10, 2015). "Pharmaceutical Drug," located at <http://en.wikipedia.org/wiki/Pharmaceutical_drug>, last visited on Apr. 10, 2015, eleven pages.
Australian Opposition mailed on Dec. 11, 2014, against Australian Patent Application No. 2012296622, filed by Alphapharm Pty Ltd., twelve pages.
Colombian Opposition mailed on May 28, 2014, against Colombian Patent Application No. 14029801, filed by Tecnoquimicas S.A., Thirty-Five pages.
Colombian Opposition mailed on May 29, 2014, against Colombian Patent Application No. 14029801, filed by Laboratorio Franco Colombiano S.A.S. Lafrancol SAS, Fifteen pages.
Colombian Office Action mailed on May 22, 2015, for Colombian Patent Application No. 14029801, filed on Aug. 15, 2012, Thirty-Two pages.
Costa Rican Opposition mailed on Sep. 24, 2014, against Costa Rican Patent Application No. 2014-0072, filed by Asociación de Genéricos Farmacéuticos, sixteen pages.
Ecuadorian Opposition mailed Apr. 10, 2015, against Ecuadorian Patent Application No. SP1413206, filed by Asociacion de Laboratorios Farmaceuticos (ALAFAR), Twenty-Two pages.
U.S. Appl. No. 14/817,068, filed Aug. 3, 2015, by Desai et al.
U.S. Appl. No. 14/828,406, filed Aug. 17, 2015, by Desai et al.
AIDS Healthcare Foundation, Inc. Complaint for Declaratory Judgment of Patent Invalidity and Violation of the Sherman Act, 15 U.S.C. §§ 1 and 2 against Gilead Sciences, Inc., Japan Tobacco, Inc., Japan Tobacco International U.S.A., Inc., and Emory University dated Jan. 26, 2016 for Case No. 3:16-cv-00443, thirty-three pages.
Israeli Opposition mailed on Dec. 22, 2015, against Israeli Patent Application No. 230949, filed by Teva Pharmaceutical Industries Ltd., three pages.

TENOFOVIR ALAFENAMIDE HEMIFUMARATE

CROSS-REFERENCE TO RELATED APPLICATIONS

This application is a continuation of application Ser. No. 13/586,358 filed Aug. 15, 2012, which in turn claims the benefit of priority from U.S. Provisional Patent Application No. 61/524,224, filed Aug. 16, 2011, the content of each of which is hereby incorporated by reference herein in its entirety.

BACKGROUND OF THE INVENTION

Description of Related Art

U.S. Pat. Nos. 7,390,791 and 7,803,788 (the content of each of which is incorporated by reference herein in its entirety) describe certain prodrugs of phosphonate nucleotide analogs that are useful in therapy. One such prodrug is 9-[(R)-2-[[(S)-[[(S)-1-(isopropoxycarbonyl)ethyl]amino]phenoxyphosphinyl]methoxy]propyl]adenine. This compound is also known by the Chemical Abstract name L-alanine, N—[(S)-[[(1R)-2-(6-amino-9H-purin-9-yl)-1-methylethoxy]methyl]phenoxyphosphinyl]-, 1-methylethyl ester. U.S. Pat. Nos. 7,390,791 and 7,803,788 also disclose a monofumarate form of this compound and its preparation method (see, e.g., Example 4).

SUMMARY OF THE INVENTION

Described is a hemifumarate form of 9-[(R)-2-[[(S)-[[(S)-1-(isopropoxycarbonyl)ethyl]amino]phenoxyphosphinyl]methoxy]propyl]adenine. The name for 9-[(R)-2-[[(S)-[[(S)-1-(isopropoxycarbonyl)ethyl]amino]phenoxyphosphinyl]methoxy]propyl]adenine is tenofovir alafenamide. The hemifumarate form of tenofovir alafenamide is also referred to herein as tenofovir alafenamide hemifumarate.

In one embodiment of the invention is provided tenofovir alafenamide hemifumarate.

In another embodiment is provided tenofovir alafenamide hemifumarate, wherein the ratio of fumaric acid to tenofovir alafenamide is 0.5±0.1, or 0.5±0.05, or 0.5±0.01, or about 0.5.

In one embodiment is provided tenofovir alafenamide hemifumarate in a solid form.

In one embodiment is provided tenofovir alafenamide hemifumarate that has an X-ray powder diffraction (XRPD) pattern having 2theta values of 6.9±0.2° and 8.6±0.2°. In another embodiment is provided tenofovir alafenamide hemifumarate wherein the XRPD pattern comprises 2theta values of 6.9±0.2°, 8.6±0.2°, 11.0±0.2°, 15.9±0.2°, and 20.2±0.2°.

In one embodiment is provided tenofovir alafenamide hemifumarate that has a differential scanning calorimetry (DSC) onset endotherm of 131±2° C., or 131±1° C.

In one embodiment is provided a pharmaceutical composition comprising tenofovir alafenamide hemifumarate and a pharmaceutically acceptable excipient. In another embodiment is provided the pharmaceutical composition, further comprising an additional therapeutic agent. In a further embodiment, the additional therapeutic agent is selected from the group consisting of human immunodeficiency virus (HIV) protease inhibiting compounds, HIV nonnucleoside inhibitors of reverse transcriptase, HIV nucleoside inhibitors of reverse transcriptase, HIV nucleotide inhibitors of reverse transcriptase, HIV integrase inhibitors, and CCR5 inhibitors.

In one embodiment is provided a method for treating a human immunodeficiency virus (HIV) infection comprising administering to a subject in need thereof a therapeutically effective amount of tenofovir alafenamide hemifumarate. In another embodiment is provided a method for treating an HIV infection comprising administering to a subject in need thereof a therapeutically effective amount of a pharmaceutical composition comprising tenofovir alafenamide hemifumarate. In a further embodiment, the method comprises administering to the subject one or more additional therapeutic agents selected from the group consisting of HIV protease inhibiting compounds, HIV nonnucleoside inhibitors of reverse transcriptase, HIV nucleoside inhibitors of reverse transcriptase, HIV nucleotide inhibitors of reverse transcriptase, HIV integrase inhibitors, and CCR5 inhibitors.

In one embodiment is provided a method for treating a hepatitis B virus (HBV) infection comprising administering to a subject in need thereof a therapeutically effective amount of tenofovir alafenamide hemifumarate. In another embodiment is provided a method for treating an HBV infection comprising administering to a subject in need thereof a therapeutically effective amount of the pharmaceutical composition comprising tenofovir alafenamide hemifumarate.

In one embodiment is provided a method for preparing a pharmaceutical composition comprising combining tenofovir alafenamide hemifumarate and a pharmaceutically acceptable excipient to provide the pharmaceutical composition.

In one embodiment is provided a method for preparing tenofovir alafenamide hemifumarate comprising subjecting a solution comprising a suitable solvent; fumaric acid; tenofovir alafenamide; and, optionally, one or more seeds of tenofovir alafenamide hemifumarate to conditions that provide for the crystallization of the fumaric acid and the tenofovir alafenamide. In one embodiment, the solvent comprises acetonitrile. In another embodiment, the solution is subjected to a temperature in the range of from about 0° C. to about 75° C.

In one embodiment is provided tenofovir alafenamide hemifumarate for use in medical therapy.

In one embodiment is provided the use of tenofovir alafenamide hemifumarate for the prophylactic or therapeutic treatment of an HIV infection. In another embodiment is provided the use of tenofovir alafenamide hemifumarate to treat an HIV infection. In a further embodiment is provided the use of tenofovir alafenamide hemifumarate for the preparation or manufacture of a medicament for the treatment of an HIV infection. In another further embodiment is provided tenofovir alafenamide hemifumarate for use in treating an HIV infection.

In one embodiment is provided the use of tenofovir alafenamide hemifumarate for the prophylactic or therapeutic treatment of an HBV infection. In another embodiment is provided the use of tenofovir alafenamide hemifumarate to treat an HBV infection. In a further embodiment is provided the use of tenofovir alafenamide hemifumarate for the preparation or manufacture of a medicament for the treatment of an HBV infection. In another further embodiment is provided tenofovir alafenamide hemifumarate for use in treating an HBV infection.

In some embodiments of the invention, the methods of treating and the like comprise administration of multiple daily doses. In other embodiments, the methods of treating and the like comprise administration of a single daily dose.

In one embodiment of the invention is provided a composition consisting essentially of tenofovir alafenamide hemifumarate.

BRIEF DESCRIPTIONS OF THE DRAWINGS

DETAILED DESCRIPTION OF THE INVENTION

Figure 1:
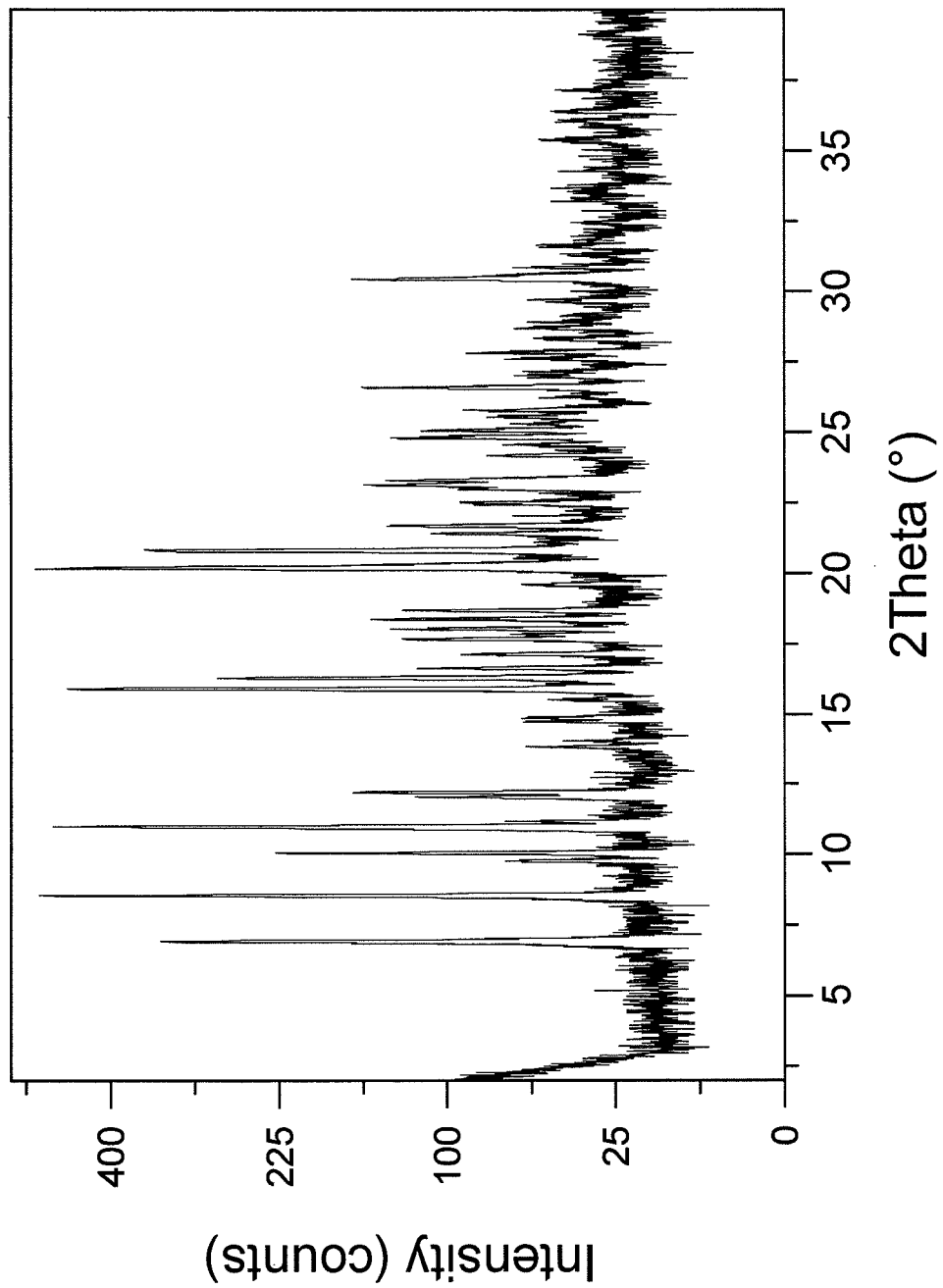
FIG. 1 shows the X-ray powder diffraction (XRPD) pattern of tenofovir alafenamide hemifumarate.

Specific values listed within the present description for radicals, substituents, and ranges are for illustration only; they do not exclude other defined values or other values within defined ranges for the radicals and substituents.

In one embodiment, there is provided a hemifumarate form of tenofovir alafenamide (i.e., tenofovir alafenamide hemifumarate). This form may have a ratio (i.e., a stoichiometric ratio or mole ratio) of fumaric acid to tenofovir alafenamide of 0.5±0.1, 0.5±0.05, 0.5±0.01, or about 0.5, or the like.

In one embodiment, tenofovir alafenamide hemifumarate consists of fumaric acid and tenofovir alafenamide in a ratio of 0.5±0.1.

In one embodiment, tenofovir alafenamide hemifumarate consists essentially of fumaric acid and tenofovir alafenamide in a ratio of 0.5±0.1.

In one embodiment, tenofovir alafenamide hemifumarate has an XRPD pattern comprising 2theta values of 6.9±0.2°, 8.6±0.2°, 10.0±0.2°, 11.0±0.2°, 12.2±0.2°, 15.9±0.2°, 16.3±0.2°, 20.2±0.2°, and 20.8±0.2°.

In one embodiment, tenofovir alafenamide hemifumarate has an XRPD pattern comprising at least four 2theta values selected from 6.9±0.2°, 8.6±0.2°, 10.0±0.2°, 11.0±0.2°, 12.2±0.2°, 15.9±0.2°, 16.3±0.2°, 20.2±0.2°, and 20.8±0.2°.

In one embodiment, tenofovir alafenamide hemifumarate has a DSC onset endotherm of 131±2° C., or 131±1° C.

In one embodiment, a tenofovir alafenamide hemifumarate composition comprises less than about 5% by weight of tenofovir alafenamide monofumarate.

In one embodiment, a tenofovir alafenamide hemifumarate composition comprises less than about 1% by weight of tenofovir alafenamide monofumarate.

In one embodiment, a tenofovir alafenamide hemifumarate composition comprises less than about 0.5% by weight of tenofovir alafenamide monofumarate.

In one embodiment, a tenofovir alafenamide hemifumarate composition comprises no detectable tenofovir alafenamide monofumarate.

Tenofovir alafenamide (i.e., the compound 9-[(R)-2-[[(S)-[[(S)-1-(isopropoxycarbonyl)ethyl]amino]phenoxyphosphinyl]methoxy]propyl]adenine) can be prepared as described in U.S. Pat. No. 7,390,791.

Selective Crystallization

In one embodiment, tenofovir alafenamide hemifumarate can be prepared using selective crystallization. An example of a scheme for this preparation method is as follows.

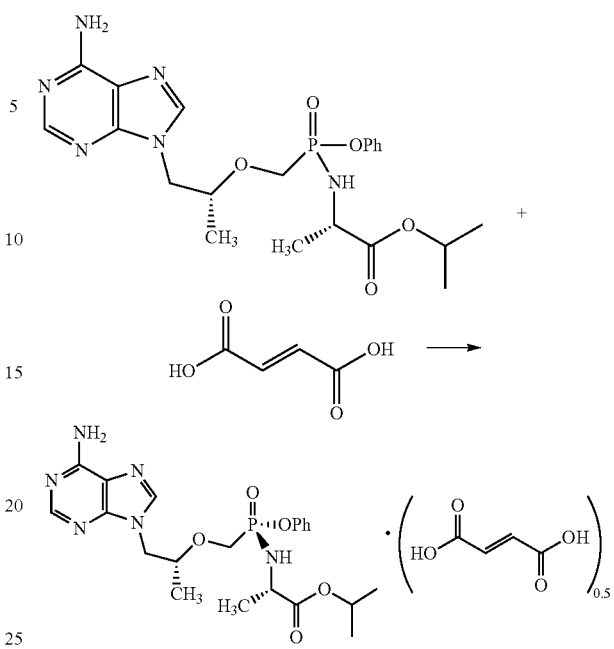

The method can be carried out by subjecting a solution comprising: a) a suitable solvent; b) fumaric acid; c) tenofovir alafenamide; and, optionally, d) one or more seeds comprising tenofovir alafenamide hemifumarate, to conditions that provide for the crystallization of fumaric acid and tenofovir alafenamide. The starting solution can contain the single diastereomer of tenofovir alafenamide or a mixture of tenofovir alafenamide and one or more of its other diastereomers (e.g., GS-7339, as described in U.S. Pat. No. 7,390,791).

The selective crystallization can be carried out in any suitable solvent. For example, it can be carried out in a protic solvent or in an aprotic organic solvent, or in a mixture thereof. In one embodiment, the solvent comprises a protic solvent (e.g., water or isopropyl alcohol). In another embodiment, the solvent comprises an aprotic organic solvent (e.g., acetone, acetonitrile (ACN), toluene, ethyl acetate, isopropyl acetate, heptane, tetrahydrofuran (THF), 2-methyl THF, methyl ethyl ketone, or methyl isobutyl ketone, or a mixture thereof). In one embodiment, the solvent comprises ACN or a mixture of ACN and up to about 50% methylene chloride (by volume). The selective crystallization also can be carried out at any suitable temperature, for example, a temperature in the range of from about 0° C. to about 70° C. In one specific embodiment, the resolution is carried out at a temperature of about 0° C.

One major advantage of the hemifumarate form of tenofovir alafenamide over the monofumarate form is its exceptional capability to purge GS-7339 (i.e., 9-[(R)-2-[[(R)-[[(S)-1-(isopropoxycarbonyl)ethyl]amino]phenoxyphosphinyl]methoxy]propyl]adenine; described in, e.g., U.S. Pat. No. 7,390,791), which is the major diastereomeric impurity in the active pharmaceutical ingredient. Thus, the hemifumarate form of tenofovir alafenamide can be more readily and easily separated from impurities than the monofumarate form. Other major advantages of tenofovir alafenamide hemifumarate over the monofumarate form include improved thermodynamic and chemical stability (including long-term storage stability), superior process reproducibility, superior drug product content uniformity, and a higher melting point.

Tenofovir alafenamide hemifumarate is useful in the treatment and/or prophylaxis of one or more viral infections in man or animals, including infections caused by DNA viruses. RNA viruses, herpesviruses (e.g., CMV, HSV 1, HSV 2, VZV), retroviruses, hepadnaviruses (e.g., HBV), papillomavirus, hantavirus, adenoviruses and HIV. U.S. Pat. No. 6,043,230 (incorporated by reference herein in its entirety) and other publications describe the antiviral specificity of nucleotide analogs, such as tenofovir disoproxil. Like tenofovir disoproxil, tenofovir alafenamide is another prodrug form of tenofovir, and can be used in the treatment and/or prophylaxis of the same conditions.

Tenofovir alafenamide hemifumarate can be administered by any route appropriate to the condition to be treated. Suitable routes include oral, rectal, nasal, topical (including ocular, buccal, and sublingual), vaginal, and parenteral (including subcutaneous, intramuscular, intravenous, intradermal, intrathecal, and epidural). Generally, tenofovir alafenamide hemifumarate is administered orally, but it can be administered by any of the other routes noted herein.

Accordingly, pharmaceutical compositions include those suitable for topical or systemic administration, including oral, rectal, nasal, buccal, sublingual, vaginal, or parenteral (including subcutaneous, intramuscular, intravenous, intradermal, intrathecal, and epidural) administration. The formulations are in unit dosage form and are prepared by any of the methods well known in the art of pharmacy.

For oral therapeutic administration, the tenofovir alafenamide hemifumarate may be combined with one or more excipients and used in the form of ingestible tablets, buccal tablets, troches, capsules, elixirs, suspensions, syrups, wafers, and the like. Such pharmaceutical compositions and preparations will typically contain at least 0.1% of tenofovir alafenamide hemifumarate. The percentage of this active compound in the compositions and preparations may, of course, be varied and may conveniently be between about 2% to about 60% or more of the weight of a given unit dosage form. The amount of active compound in such therapeutically useful pharmaceutical compositions is preferably such that an effective dosage level will be obtained upon administration of a single-unit dosage (e.g., tablet). Other dosage formulations may provide therapeutically effective amounts of tenofovir alafenamide hemifumarate upon repeated administration of subclinically effective amounts of the same. Preferred unit dosage formulations include those containing a daily dose (e.g., a single daily dose), as well as those containing a unit daily subclinical dose, or an appropriate fraction thereof (e.g., multiple daily doses), of tenofovir alafenamide hemifumarate.

Pharmaceutical compositions suitable for oral administration may be presented as discrete units such as capsules, cachets, or tablets, each containing a predetermined amount of tenofovir alafenamide hemifumarate; as a powder or granules; as a solution or a suspension in an aqueous liquid or a nonaqueous liquid; or as an oil-in-water liquid emulsion or a water-in-oil liquid emulsion. Tenofovir alafenamide hemifumarate may also be presented as a bolus, electuary, or paste.

Tenofovir alafenamide hemifumarate is preferably administered as part of a pharmaceutical composition or formulation. Such pharmaceutical composition or formulation comprises tenofovir alafenamide hemifumarate together with one or more pharmaceutically acceptable carriers/excipients, and optionally other therapeutic ingredients. The excipient(s)/carrier(s) must be "acceptable" in the sense of being compatible with the other ingredients of the formulation and not deleterious to the patient. Excipients include, but are not limited to, substances that can serve as a vehicle or medium for tenofovir alafenamide hemifumarate (e.g., a diluent carrier). They may be enclosed in hard or soft shell gelatin capsules, may be compressed into tablets, or may be incorporated directly with the food of the patient's diet.

Accordingly, the tablets, troches, pills, capsules, and the like may also contain, without limitation, the following: a binder(s), such as hydroxypropyl cellulose, povidone, or hydroxypropyl methylcellulose; a filler(s), such as microcrystalline cellulose, pregelatinized starch, starch, mannitol, or lactose monohydrate; a disintegrating agent(s), such as croscarmellose sodium, cross-linked povidone, or sodium starch glycolate; a lubricant(s), such as magnesium stearate, stearic acid, or other metallic stearates; a sweetening agent(s), such as sucrose, fructose, lactose, or aspartame; and/or a flavoring agent(s), such as peppermint, oil of wintergreen, or a cherry flavoring. When the unit dosage form is a capsule, it may contain, in addition to materials of the above types, a liquid carrier, such as a vegetable oil or a polyethylene glycol. Various other materials may be present as coatings or to otherwise modify the physical form of the solid unit dosage form. For instance, tablets, pills, or capsules may be coated with gelatin, polymers, wax, shellac, or sugar and the like. Of course, any material used in preparing any unit dosage form typically will be pharmaceutically acceptable and substantially nontoxic in the amounts employed. In addition, tenofovir alafenamide hemifumarate may be incorporated into sustained-release preparations and devices.

For infections of the eye or other external tissues, e.g., mouth and skin, the pharmaceutical compositions are preferably applied as a topical ointment or cream containing tenofovir alafenamide hemifumarate in an amount of, for example, 0.01 to 10% w/w (including active ingredient in a range between 0.1% and 5% in increments of 0.1% w/w such as 0.6% w/w, 0.7% w/w, etc.), preferably 0.2 to 3% w/w and most preferably 0.5 to 2% w/w. When formulated in an ointment, the active ingredient may be employed with either a paraffinic or a water-miscible ointment base. Alternatively, the active ingredient may be formulated in a cream with an oil-in-water cream base.

Pharmaceutical compositions suitable for topical administration in the mouth include lozenges comprising tenofovir alafenamide hemifumarate in a flavored basis, for example, sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising, for example, cocoa butter or a salicylate.

Pharmaceutical formulations suitable for parenteral administration are sterile and include aqueous and nonaqueous injection solutions that may contain antioxidants, buffers, bacteriostats, and solutes that render the formulation isotonic with the blood of the intended recipient; and aqueous and nonaqueous sterile suspensions that may include suspending agents and thickening agents. The formulations may be presented in unit-dose or multi-dose containers, for example, sealed ampoules and vials with elastomeric stoppers, and may be stored in a freeze-dried (lyophilized) condition requiring only the addition of the sterile liquid carrier (e.g., water for injections) immediately prior to use. Injection solutions and suspensions may be prepared from sterile powders, granules, and tablets of the kind previously described.

In addition to the ingredients particularly mentioned above, the pharmaceutical compositions/formulations may include other ingredients conventional in the art, having regard to the type of formulation in question.

In another embodiment, there is provided veterinary compositions comprising tenofovir alafenamide hemifumarate together with a veterinary carrier therefor. Veterinary carriers are materials useful for the purpose of administering the composition to cats, dogs, horses, rabbits, and other animals, and may be solid, liquid, or gaseous materials that are otherwise inert or acceptable in the veterinary art and are compatible with the active ingredient. These veterinary compositions may be administered orally, parenterally, or by any other desired route.

The tenofovir alafenamide hemifumarate can be used to provide controlled release pharmaceutical formulations containing a matrix or absorbent material and an active ingredient of the invention, in which the release of the active ingredient can be controlled and regulated to allow less frequent dosing or to improve the pharmacokinetic or toxicity profile of the compound. Controlled release formulations adapted for oral administration, in which discrete units comprising a compounds of the invention, can be prepared according to conventional methods.

Useful dosages of tenofovir alafenamide hemifumarate can be determined by comparing in vitro activities, and the in vivo activities in animal models. Methods for the extrapolation of effective amounts/dosages in mice and other animals to therapeutically effective amounts/dosages in humans are known in the art.

The amount of tenofovir alafenamide hemifumarate required for use in treatment will vary with several factors, including but not limited to the route of administration, the nature of the condition being treated, and the age and condition of the patient; ultimately, the amount administered will be at the discretion of the attendant physician or clinician. The therapeutically effective amount/dose of tenofovir alafenamide hemifumarate depends, at least, on the nature of the condition being treated, any toxicity or drug interaction issues, whether the compound is being used prophylactically (e.g., sometimes requiring lower doses) or against an active disease or condition, the method of delivery, and the pharmaceutical formulation, and will be determined by the clinician using conventional dose escalation studies.

In one embodiment, the oral dose of tenofovir alafenamide hemifumarate may be in the range from about 0.0001 to about 100 mg/kg body weight per day, for example, from about 0.01 to about 10 mg/kg body weight per day, from about 0.01 to about 5 mg/kg body weight per day, from about 0.5 to about 50 mg/kg body weight per day, from about 1 to about 30 mg/kg body weight per day, from about 1.5 to about 10 mg/kg body weight per day, or from about 0.05 to about 0.5 mg/kg body weight per day. As a nonlimiting example, the daily candidate dose for an adult human of about 70 kg body weight will range from about 0.1 mg to about 1000 mg, or from about 1 mg to about 1000 mg, or from about 5 mg to about 500 mg, or from about 1 mg to about 150 mg, or from about 5 mg to about 150 mg, or from about 5 mg to about 100 mg, and may take the form of single or multiple doses.

The pharmaceutical compositions described herein may further include one or more therapeutic agents in addition to tenofovir alafenamide hemifumarate. In one specific embodiment of the invention, the additional therapeutic agent can be selected from the group consisting of HIV protease inhibiting compounds, HIV nonnucleoside inhibitors of reverse transcriptase, HIV nucleoside inhibitors of reverse transcriptase, HIV nucleotide inhibitors of reverse transcriptase, HIV integrase inhibitors, and CCR5 inhibitors.

Therapeutic methods include administering tenofovir alafenamide hemifumarate to a subject/patient in need of the same as a therapeutic or preventative treatment. Thus, tenofovir alafenamide hemifumarate may be administered to a subject/patient having a medical disorder or to a subject who may acquire the disorder. One of ordinary skill will appreciate that such treatment is given in order to ameliorate, prevent, delay, cure, and/or reduce the severity of a symptom or set of symptoms of a disorder (including a recurring disorder). The treatment may also be given to prolong the survival of a subject, e.g., beyond the survival time expected in the absence of such treatment. The medical disorders that may be treated with tenofovir alafenamide hemifumarate include those discussed herein, including without limitation, HIV infection and HBV infection.

The following are nonlimiting, illustrative Examples.

EXAMPLE 1

Tenofovir alafenamide monofumarate solids (5.0 g) and 9-[(R)-2-[[(R)-[[(S)-1-(isopropoxycarbonyl)ethyl]amino]phenoxyphosphinyl]methoxy]propyl]adenine (GS-7339) monofumarate solids (0.75 g) were charged into 35 g MTBE at 22° C. and the mixture was stirred for 1 hour. A slurry was formed and was dried in a rotary evaporator. 58 g acetonitrile (ACN) was charged into the solids and the mixture was heated to reflux to dissolve the solids. The resulting solution was allowed to cool naturally while agitated. A slurry was formed, and the slurry was further cooled by ice-water-bath. The solids were isolated by filtration and washed with 5 g ACN. The solids were dried in a vacuum oven at 40° C. overnight. 5.52 g off-white solids were obtained. The solids were analyzed by XRPD and found to contain tenofovir alafenamide monofumarate, GS-7339 monofumarate, and tenofovir alafenamide hemifumarate.

EXAMPLE 2

Preparation of Tenofovir Alafenamide Hemifumarate Via Selective Crystallization

9-[(R)-2-[[[[(S)-1-(isopropoxycarbonyl)ethyl]amino]phenoxyphosphinyl]methoxy]propyl]adenine as a slurry in ACN (9.7 kg slurry, 13.8 wt %, a diastereomeric mixture of 1.0 kg (2.10 mol, 1 mol equiv) of 9-[(R)-2-[[(S)-[[(S)-1-(isopropoxycarbonyl)ethyl]amino]phenoxyphosphinyl]methoxy]propyl]adenine and 0.35 kg of 9-[(R)-2-[[(R)-[[(S)-1-(isopropoxycarbonyl)ethyl]amino]phenoxyphosphinyl]methoxy]propyl]adenine was charged into a reactor and rinsed forward with dichloromethane (5 kg). The mixture was concentrated under vacuum to about 3 L with jacket temperature below 40° C. The concentrate was then coevaporated with ACN (6 kg) under vacuum to about 3 L with jacket temperature below 40° C. The concentrate was diluted with ACN (8.5 kg) and warmed to 40-46° C. The warm mixture was filtered into a second reactor and the filtrate was cooled to 19-25° C.

To the above solution was charged fumaric acid (0.13 kg, 1.12 mol, 0.542 mole equiv) followed by ACN (1 kg), and the mixture was heated to 67-73° C. The hot mixture was transferred into a reactor via a polishing filter, and then adjusted to 54-60° C. Seed crystals (5 g) of the hemifumarate form of tenofovir alafenamide were charged (for example, the mixture can be seeded with tenofovir alafenamide hemifumarate formed in Example 1 or a subsequent production), and the resulting mixture was agitated at 54-60° C. for about 30 minutes. The mixture was cooled over a minimum of 4 hours to 0-6° C., and then agitated at 0-6° C. for a minimum of 1 hour. The resulting slurry was filtered and rinsed with chilled (0-6° C.) ACN (2 kg). The product was dried under vacuum below 45° C. until loss on drying (LOD) and organic volatile impurities (OVI) limits were met (LOD≤1.0%, dichloromethane content ≤0.19%, acetonitrile content ≤0.19%) to afford the final compound of the hemifumarate form of tenofovir alafenamide as a white to off-white powder (typical yield is about 0.95 kg). $^1$H NMR (400 MHz, d6 DMSO): δ 1.06 (d, J=5.6 Hz, 3H), 1.12-1.16 (m, 9H), 3.77 (dd, J=10.4, 11.6 Hz, 1H), 3.84-3.90 (m, 2H), 3.94 (m, 1H), 4.14 (dd, J=6.8, 14.8 Hz, 1H), 4.27 (m, 1H), 4.85 (heptet, J=6.0 Hz, 1H), 5.65 (t, J=11.2 Hz, 1H), 6.63 (s, 1H), 7.05 (d. J=7.6 Hz, 2H), 7.13 (t, J=7.2 Hz, 1H), 7.24 (s, 2H), 7.29 (t, J=7.6 Hz, 2H), 8.13 (t, J=13.6 Hz, 2H), $^{31}$P NMR (162 MHz, d6 DMSO): δ 23.3.

EXAMPLE 3

Preparation of Tenofovir Alafenamide Hemifumarate

To a jacketed reactor equipped with overhead agitator, was charged 9-[(R)-2-[[(S)-[[(S)-1-(isopropoxycarbonyl)ethyl]amino]phenoxyphosphinyl]methoxy]propyl]adenine (10 g), fumaric acid (1.22 g), and ACN (100 mL). The mixture was heated to 70-75° C. to dissolve the solids. Any undissolved particulates were removed by filtration through a cartridge filter. The filtered solution was cooled to 60-65° C., and seeded with 1% (by weight) of tenofovir alafenamide hemifumarate. The slurry was aged for 30 minutes and cooled to 0-5° C. over 2 hours. The temperature was maintained for 1-18 hours, and the resulting slurry was filtered and washed with 2 ml of cold ACN (0-5° C.). The solids were dried under vacuum at 50° C. to provide the hemifumarate form of tenofovir alafenamide, which was characterized as described below.

Characterization of Tenofovir Alafenamide Hemifumarate from Example 3

Tenofovir alafenamide hemifumarate from Example 3 consists of 9-[(R)-2-[[(S)-[[(S)-1-(isopropoxycarbonyl)ethyl]amino]phenoxyphosphinyl]methoxy]propyl]adenine and one-half an equivalent of fumaric acid. Tenofovir alafenamide hemifumarate is anhydrous, nonhygroscopic, and has a DSC onset endotherm of about 131° C.

X-Ray Powder Diffraction

The XRPD pattern of tenofovir alafenamide hemifumarate was obtained in the following experimental setting: 45 KV, 45 mA, Kα1=1.5406 Å, scan range 2.-40°, step size 0.0084°, counting time: 8.25 s. The XRPD pattern for tenofovir alafenamide hemifumarate is shown in FIG. 1. The characteristic peaks include: 6.9±0.2°, 8.6±0.2°, 10.0±0.2°, 11.0±0.2°, 12.2±0.2°, 15.9±0.2°, 16.3±0.2°, 20.2±0.2°, and 20.8±0.2°.

Single-Crystal X-Ray Diffraction

The crystal size was 0.32×0.30×0.20 mm$^3$. The sample was held at 123 K and the data was collected using a radiation source with a wavelength of 0.71073 Å in the theta range of 1.59 to 25.39°. Conditions of, and data collected from the single-crystal X-ray diffraction are shown in Table 1.

TABLE 1

| Single-Crystal X-ray Diffraction | |
| --- | --- |
| Empirical formula | $C_{23}H_{31}N_6O_7P$ |
| Formula weight | 534.50 |
| Temperature | 123(2) K |
| Crystal size | 0.32 × 0.30 × 0.20 mm$^3$ |
| Theta range for data collection | 1.59 to 25.39° |
| Wavelength | 0.71073 Å |
| Crystal system | Tetragonal |
| Space group | P4(2)2(1)2 |

TABLE 1-continued

| Single-Crystal X-ray Diffraction | | |
| --- | --- | --- |
| Unit cell dimensions | a = 18.1185(12) Å | α = 90° |
| | b = 18.1185(12) Å | β = 90° |
| | c = 17.5747(11) Å | γ = 90° |
| Volume | 5769.4(6) Å$^3$ | |
| Z | 8 | |
| Density (calculated) | 1.231 g/cm$^3$ | |

DSC Analysis

Figure 2:
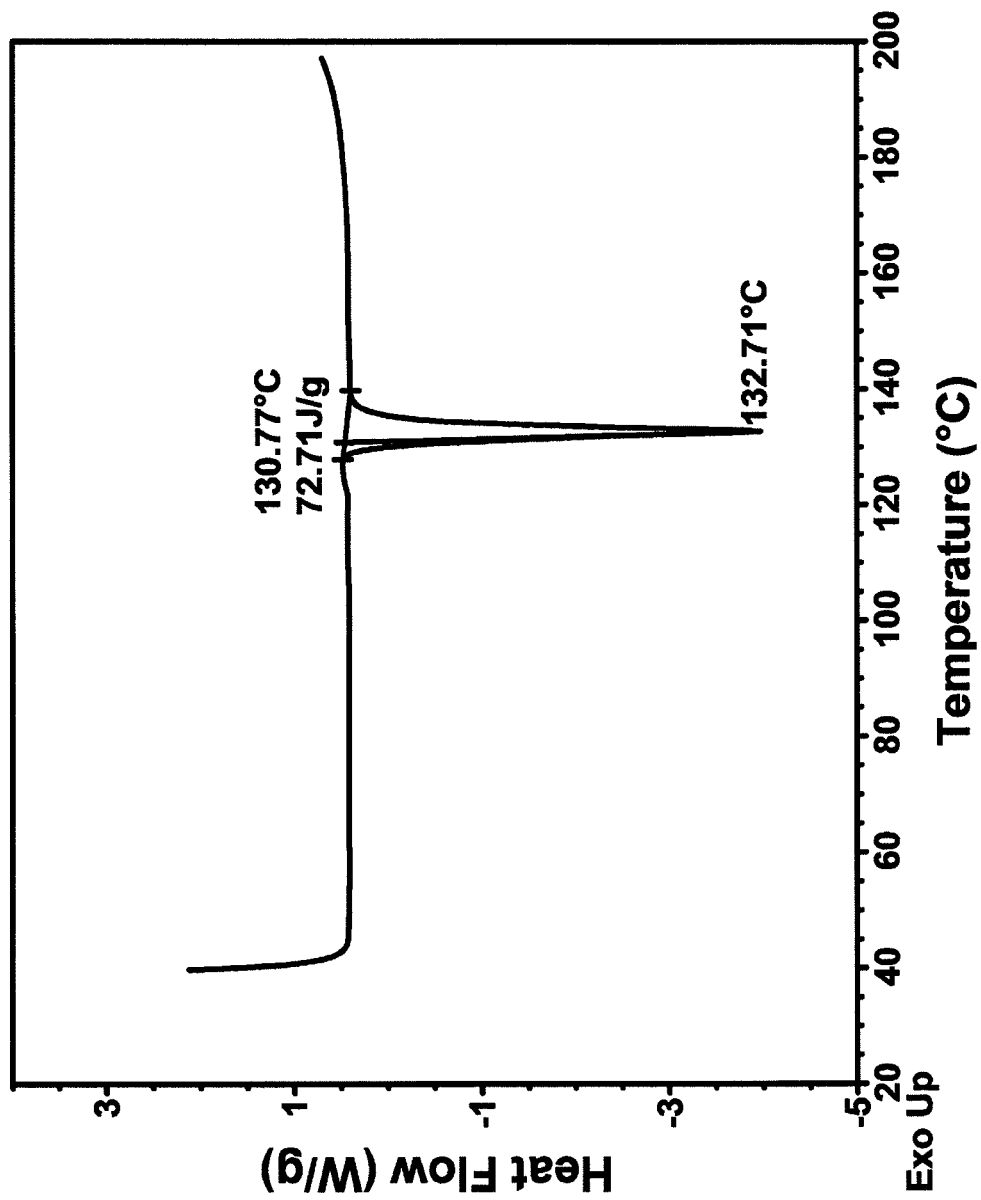
FIG. 2 shows a graph of the DSC analysis of tenofovir alafenamide hemifumarate.

The DSC analysis was conducted using 2.517 mg of tenofovir alafenamide hemifumarate. It was heated at 10° C./min over the range of 40-200° C. The onset endotherm was found to be about 131° C. (FIG. 2).

TGA Data

Figure 3:
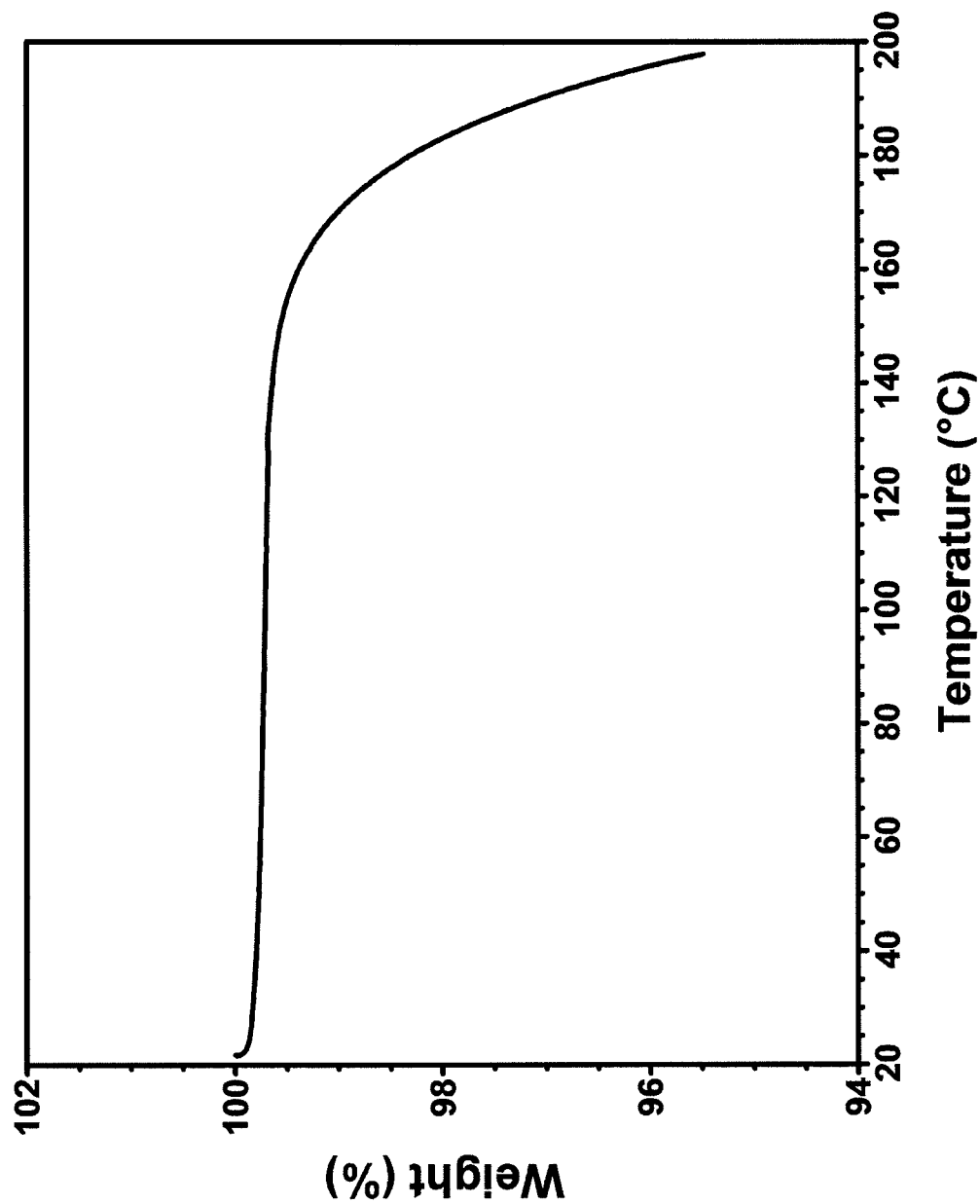
FIG. 3 shows a graph of the thermogravimetric analysis (TGA) data for tenofovir alafenamide hemifumarate.

The TGA data were obtained using 4.161 mg of tenofovir alafenamide hemifumarate. It was heated at 10° C./min over the range of 25-200° C. The sample lost 0.3% weight before melting (FIG. 3). It was determined to be an anhydrous form.

DVS Analysis

Figure 4:
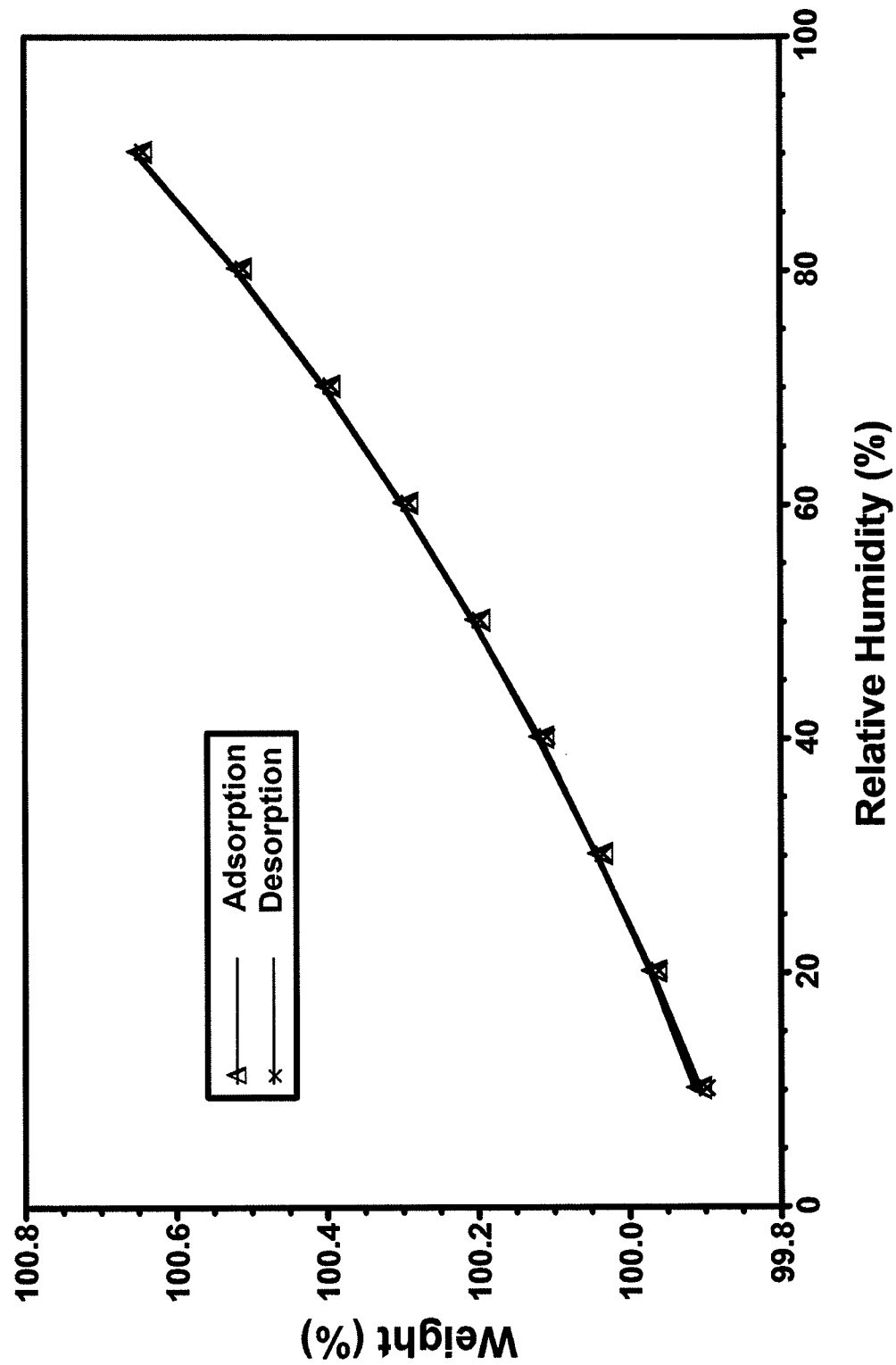
FIG. 4 shows a graph of the dynamic vapor sorption (DVS) analysis of tenofovir alafenamide hemifumarate.

DVS analysis was conducted using 4.951 mg of tenofovir alafenamide hemifumarate. The material was kept at 25° C. in nitrogen at humidities ranging from 10% to 90% relative humidity; each step was equilibrated for 120 minutes. The sorption isotherm is shown at FIG. 4. The material was found to be nonhygroscopic, and to absorb 0.65% water at a relative humidity of 90%.

Purging of Diastereomeric Impurity

In the prior syntheses of tenofovir alafenamide, one of the major impurities is typically the diastereomer 9-[(R)-2-[[(R)-[[(S)-1-(isopropoxycarbonyl)ethyl]amino]phenoxyphosphinyl]methoxy]propyl]adenine. The hemifumarate form of tenofovir alafenamide from Example 3 has an exceptional capability to purge this diastereomeric impurity, as compared with the capability of the monofumarate form (described in U.S. Pat. No. 7,390,791). The data in Table 2 (below) demonstrates that tenofovir alafenamide hemifumarate (Batch 2) purged the diastereomeric impurity to less than one-tenth of the starting concentration, whereas the monofumarate form of tenofovir alafenamide (Batch 1) only slightly purged the diastereomeric impurity.

TABLE 2

| Purging Capability Comparison | | | | | |
| --- | --- | --- | --- | --- | --- |
| Batch | Diastereomeric Impurity in Starting Material | Solvent | Fumaric acid charge (mole equivalent) | Product obtained | Diastereomeric Impurity in Product |
| 1 | 9.3% | ACN | 0.9 | Monofumarate form | 7.6% |
| 2 | 10.0% | ACN | 0.5 | Hemifumarate form | 0.65% |

Chemical Stability

Chemical stability of the hemifumarate form of tenofovir alafenamide was compared with the monofumarate form. As shown in Table 3 (below), under identical conditions, the hemifumarate form of tenofovir alafenamide was chemically more stable and exhibited better long-term storage stability, with significantly less degradation (% Total Deg. Products) than the monofumarate form. Conditions evaluated include temperature, relative humidity (RH), and the open or closed state of the container cap.

TABLE 3

Chemical Stability Comparison

| Storage Condition | Time Points (weeks) | Monofumarate form | | Hemifumarate form | |
|---|---|---|---|---|---|
| | | % TA* Area Normalized | % Total Deg. Products | % TA Area Normalized | % Total Deg. Products |
| 40° C./ 75% RH Cap Closed | 0 | 97.1 | 0.69 | 98.4 | 0.05 |
| | 1 | 97.0 | 0.87 | 98.4 | 0.14 |
| | 2 | 96.6 | 1.18 | 98.5 | 0.14 |
| | 4 | 96.4 | 1.49 | 98.4 | 0.25 |
| | 8 | 95.4 | 2.36 | 98.0 | 0.49 |
| 40° C./ 75% RH Cap Open | 0 | 97.1 | 0.69 | 98.4 | 0.05 |
| | 1 | 96.9 | 0.90 | 98.5 | 0.15 |
| | 2 | 96.6 | 1.10 | 98.5 | 0.14 |
| | 4 | 96.2 | 1.67 | 98.4 | 0.26 |
| | 8 | 95.0 | 2.74 | 98.1 | 0.50 |
| 70° C. Cap Closed | 0 | 97.1 | 0.69 | 98.4 | 0.05 |
| | 2 | 96.2 | 1.83 | 98.5 | 0.22 |
| | 4 | 93.3 | 4.78 | 98.4 | 0.33 |

*TA is tenofovir alafenamide

Thermodynamic Stability

Stable form screening of tenofovir alafenamide hemifumarate showed that it is thermodynamically stable in most solvents, such as ACN, toluene, ethyl acetate, methyl tert-butyl ether (MTBE), acetone, THF, and 2-methyl THF. A similar stable form screening of the monofumarate form showed that this form is not thermodynamically stable in the above-listed solvents. When suspended in these solvents, the monofumarate form of tenofovir alafenamide fully converts to the hemifumarate form in THF and 2-methyl THF, and partially converts to the hemifumarate form in ACN, ethyl acetate, MTBE, and acetone, as well as at ambient temperatures.

Thermal Stability

As shown by the DSC data, the hemifumarate form of tenofovir alafenamide has a melting point that is about 10° C. higher than that of the monofumarate form, indicating that the hemifumarate form has improved thermal stability as compared with the monofumarate form.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A composition comprising tenofovir alafenamide hemifumarate, wherein the composition comprises less than about 5% by weight of tenofovir alafenamide monofumarate.

2. The composition of claim 1, wherein the composition comprises less than about 1% by weight of tenofovir alafenamide monofumarate.

3. The composition of claim 1, wherein the composition comprises less than about 0.5% by weight of tenofovir alafenamide monofumarate.

4. The composition of claim 1, wherein the ratio of fumaric acid to tenofovir alafenamide in said composition is 0.5±0.1.

5. The composition of claim 1, wherein the ratio of fumaric acid to tenofovir alafenamide in said composition is 0.5±0.01.

6. The composition of claim 1, having an X-ray powder diffraction pattern that comprises 2theta values of 6.9±0.2° and 8.6±0.2°.

7. A pharmaceutical composition comprising the composition of claim 1 and a pharmaceutically acceptable excipient.

8. The pharmaceutical composition of claim 7, further comprising an additional therapeutic agent.

9. The pharmaceutical composition of claim 8, wherein the additional therapeutic agent is selected from the group consisting of human immunodeficiency virus (HIV) protease inhibiting compounds, HIV nonnucleoside inhibitors of reverse transcriptase, HIV nucleoside inhibitors of reverse transcriptase, HIV nucleotide inhibitors of reverse transcriptase, HIV integrase inhibitors, and CCR5 inhibitors.

10. A method for treating a human immunodeficiency virus (HIV) infection comprising administering to a subject in need thereof a therapeutically effective amount of the composition of claim 1.

11. A method for treating an HIV infection comprising administering to a subject in need thereof a therapeutically effective amount of the pharmaceutical composition of claim 7.

12. The method for treating an HIV infection of claim 10, further comprising administering to the subject one or more additional therapeutic agents selected from the group consisting of human immunodeficiency virus (HIV) protease inhibiting compounds, HIV nonnucleoside inhibitors of reverse transcriptase, HIV nucleoside inhibitors of reverse transcriptase, HIV nucleotide inhibitors of reverse transcriptase, HIV integrase inhibitors, and CCR5 inhibitors.

13. A method for treating a hepatitis B virus (HBV) infection comprising administering to a subject in need thereof a therapeutically effective amount of the composition of claim 1.

14. A method for treating an HBV infection comprising administering to a subject in need thereof a therapeutically effective amount of the pharmaceutical composition of claim 7.

15. A method for preparing a pharmaceutical composition comprising combining the composition of claim 1 and a pharmaceutically acceptable excipient to provide the pharmaceutical composition.

16. The method for treating an HIV infection of claim 10, wherein the composition is administered in multiple daily doses.

17. The method for treating an HIV infection of claim 10, wherein the composition is administered in a single daily dose.

18. The method for treating an HBV infection of claim 13, wherein the composition is administered in multiple daily doses.

19. The method for treating an HBV infection of claim 13, wherein the composition is administered in a single daily dose.

* * * * *